US009844515B2

(12) United States Patent
Fleschhut et al.

(10) Patent No.: US 9,844,515 B2
(45) Date of Patent: Dec. 19, 2017

(54) TRANSDERMAL THERAPEUTIC SYSTEM COMPRISING BUPRENORPHINE

(75) Inventors: Jens Fleschhut, Holzkirchen (DE); Susanne Feinaeugle, Holzkirchen (DE); Karin Lauer, Holzkirchen (DE)

(73) Assignee: Hexal AG, Holzkirchen (DE)

( * ) Notice: Subject to any disclaimer, the term of this patent is extended or adjusted under 35 U.S.C. 154(b) by 335 days.

(21) Appl. No.: 13/885,958

(22) PCT Filed: Nov. 17, 2011

(86) PCT No.: PCT/EP2011/005784
§ 371 (c)(1),
(2), (4) Date: Jun. 6, 2013

(87) PCT Pub. No.: WO2012/065740
PCT Pub. Date: May 24, 2012

(65) Prior Publication Data
US 2013/0331803 A1 Dec. 12, 2013

(30) Foreign Application Priority Data
Nov. 17, 2010 (EP) ..................................... 10014713

(51) Int. Cl.
| | | |
|---|---|---|
| *A61F 13/00* | (2006.01) | |
| *A61K 9/70* | (2006.01) | |
| *A61K 31/485* | (2006.01) | |
| *A61K 47/12* | (2006.01) | |
| *A61K 47/14* | (2017.01) | |

(52) U.S. Cl.
CPC .......... *A61K 9/7069* (2013.01); *A61K 9/7061* (2013.01); *A61K 31/485* (2013.01); *A61K 47/12* (2013.01); *A61K 47/14* (2013.01)

(58) Field of Classification Search
CPC .. A61K 9/7069; A61K 9/7061; A61K 31/485; A61K 47/14; A61K 47/12
See application file for complete search history.

(56) References Cited

U.S. PATENT DOCUMENTS

| | | | |
|---|---|---|---|
| 5,240,711 A * | 8/1993 | Hille et al. .................... 424/448 |
| 5,683,711 A | 11/1997 | Fischer et al. | |
| 5,700,480 A | 12/1997 | Hille et al. | |
| 6,231,886 B1 | 5/2001 | Reder et al. | |
| 6,264,980 B1 | 7/2001 | Hille | |
| 6,344,211 B1 | 2/2002 | Hille | |
| 2005/0249792 A1 | 11/2005 | Kugelmann | |

FOREIGN PATENT DOCUMENTS

| | | |
|---|---|---|
| DE | 10 2004 020 463 A1 | 11/2005 |
| EP | 0 430 019 A2 | 6/1991 |
| EP | 0 819 438 A2 | 1/1998 |
| EP | 1 718 258 B1 | 11/2006 |
| WO | WO 98/36728 A2 | 8/1998 |

OTHER PUBLICATIONS

International Search Report issued in PCT/EP2011/005784, dated Jul. 5, 2012, 4 pages.
European Decision to Grant EP Patent dated Dec. 4, 2014 issued in European Patent Application No. 11784951 (EP Patent No. 2640389).
Mundipharma Pharmaceuticals Ltd., "BuTrans transdermal patches—Summary of Product Characteristics (SPC)" pp. 1-10 (Aug. 2015).
Norspan Transdermal Patch Product Information, pp. 1-4 (Aug. 2009).
Notice of Opposition to a EP Patent dated Sep. 30, 2015 issued in European Patent No. 2640389.
Declaration of Govenlock submitted in Opposition Proceeding relating to AU Patent Application No. 2011331511.
Declaration of Pouton submitted in Opposition Proceeding relating to AU Patent Application No. 2011331511.
Declaration of Roberts submitted in Opposition Proceeding relating to AU Patent Application No. 2011331511.
ASTM International, Designation: D2765-01, "Standard Test Methods for Determination of Gel Content and Swell Ratio of Crosslinked Ethylene Plastics," Apr. 2006, pp. 1-8.
Z. Czech et al., "The crosslinking reaction of acrylic PSA using chelate metal acetylacetonates", European Polymer Journal 42 [2006] 2153-2160.

\* cited by examiner

*Primary Examiner* — Hasan Ahmed
(74) *Attorney, Agent, or Firm* — Arent Fox LLP

(57) ABSTRACT

The invention is concerned with a transdermal therapeutic system (TTS) comprising buprenorphine and a method of manufacturing such a TTS. The transdermal therapeutic system is used for the transdermal administration of buprenorphine and analogues thereof. In particular, the invention relates to the use of a transdermal therapeutic system (TTS) for analgesic purposes. The TTS according to the invention comprises a transdermal drug delivery composition comprising buprenorphine and an adhesive component, which is a mixture of a crosslinked and a non-crosslinked acrylic polymer and a penetration enhancer comprising a keto acid.

7 Claims, 2 Drawing Sheets

TRANSDERMAL THERAPEUTIC SYSTEM COMPRISING BUPRENORPHINE

CROSS-REFERENCE TO RELATED APPLICATION

This application is a National Stage entry of International Application No. PCT/EP2011/005784, filed Nov. 17, 2011, which claims priority to European Application No. 10014713.1, filed Nov. 17, 2010, the entire specifications, claims and drawings of which are incorporated herewith by reference.

The invention is concerned with a transdermal therapeutic system (TTS) comprising buprenorphine. The invention further relates to a method of manufacture of a TTS comprising buprenorphine. The transdermal therapeutic system is used for the transdermal administration of buprenorphine and analogues thereof. In particular, the invention relates to the use of a transdermal therapeutic system (TTS) for analgesic purposes.

GENERAL REMARKS

Buprenorphine is a thebaine derivative with powerful analgesia, approximately twenty-five to forty times as potent as morphine. Its analgesic effect is due to partial agonist activity at μ-opioid receptors. Buprenorphine is commonly administered by intramuscular injection, intravenous infusion, via a transdermal patch, as a sublingual tablet or an ethanolic liquid oral solution. Depending on the application form, buprenorphine is indicated for the treatment of moderate to severe chronic pain or for peri-operative analgesia. Buprenorphine as analgesic, however, has the drawback that it is not suitable for oral administration, due to very high first-pass metabolism. For the treatment of chronic pain, the transdermal formulations are thus preferred, which can be used both for chronic cancer pain as well as chronic non-malignant pain, such as musculoskeletal and neuropathic pain. To control the delivery of buprenorphine and to enable a constant release of the drug to the patient, transdermal matrix systems have been shown to be particularly useful for buprenorphine administration.

Transdermal delivery systems and more specifically transdermal therapeutic systems which are also referred to herein as TTS, such as transdermal patches, have been proven to be advantageous in the administration and delivery of pharmaceutically active agents, such as buprenorphine. One of the reasons for this is that transdermal delivery systems avoid hepatic metabolization of the pharmaceutically active agent, which is frequently observed upon oral administration of a pharmaceutically active agent. As a consequence, upon administration of a pharmaceutically active agent through a transdermal delivery system the liver is relieved and gastrointestinal side effects are avoided. Additionally, compared to a non-transdermal administration, usually less of the pharmaceutically active agent is required so as to have the same effect. Furthermore, transdermal delivery systems provide a more constant blood level of the pharmaceutically active agent as said agent is immediately effective in a systemic manner upon permeation through the skin. Finally, transdermal delivery systems increase patients' compliance due to their easy and convenient application.

Commercially available classes of pressure sensitive adhesives (PSA) for use in skin contact applications such as TTS are acrylic polymers, polyisobutylene polymers (PIB) and silicone polymers. Common transdermal delivery systems, however, have the disadvantage that they often do not provide sufficient adhesive power to remain attached to a patient's skin for the period of time needed for administration of the drug, which can be from three to seven days.

Buprenorphine further has the drawback that it is extremely poor in percutaneous absorbtion. Thus, it usually requires the addition of penetration enhancers, which however can cause skin irritation. Moreover, the commercially available transdermal systems for administration of buprenorphine suffer from several disadvantages. The obtained blood plasma levels of the drug are often either too low for treating severe or chronic pain, or high blood plasma levels do not remain constant for the entire period of use. Since buprenorphine patches for transdermal delivery of the drug is usually applied to last for 72 hours or longer and up to seven days, transdermal patches are needed which can act for the time required for transdermal delivery of buprenorphine to make frequent administration of new patches unnecessary.

A transdermal patch suitable for administration of buprenorphine over several days further requires that the adhesive force is sufficient to remain attached to the skin of a patient for the required period of time without causing skin irritation. The transdermal patch should further be comfortable for the patient even in long-term applications, thus also after being attached to the skin for several days.

As a consequence, a need exists for a transdermal therapeutic system for the administration of buprenorphine, having high adhesive force, provides high and constant blood plasma levels of the drug, which is comfortable to the wearer without causing skin irritation and which does not suffer from the above discussed drawbacks.

EP 0 792 145 B1 relates to the transdermal resorption of active substances such as buprenorphine from transdermal applications comprising auxiliary agents having absorption-increasing effect and which is present as a supercooled melt.

EP 0 430 019 B1 relates to transdermal therapeutic systems comprising buprenorphine in a drug containing pressure sensitive adhesive reservoir layer, which comprises a solvent for buprenorphine remaining in the system in the reservoir layer which is a compound having at least one acidic group.

OBJECT OF THE INVENTION

It is the object of the present invention to provide a TTS for the controlled release of buprenorphine, which solves the afore-mentioned problems. In particular, it is an object of the present invention to provide a TTS having strong adhesive power. It is a further object to provide a TTS for the administration of buprenorphine, which remains attached to the skin for the time of buprenorphine administration and without causing skin irritation. The object is further to provide a transdermal system, which has a high buprenorphine release and thus is effective in providing a constant drug level in the patient, which is effective in relieving pain for the entire period of use.

DESCRIPTION OF THE INVENTION

The inventors have surprisingly found that a TTS for the administration of buprenorphine comprising an adhesive layer comprising a crosslinked acrylic polymer and a non-crosslinked acrylic polymer and further comprising a penetration enhancer comprising a keto acid solves the above problems. Such a TTS is particularly useful for providing a constant blood plasma level of the active ingredient and continuous drug delivery for more than three days (>72 h)

and preferably more than four days (>96 h) while at the same time providing optimum adhesive power and greatest comfort to the patient for the entire period of use.

The above-mentioned objects have thus been surprisingly solved in the present invention by the provision of a transdermal therapeutic system comprising
1) optionally a backing layer,
2) at least one drug containing adhesive layer containing a transdermal drug delivery composition comprising
   i. 1 to 20% by weight of buprenorphine or a pharmaceutically acceptable salt thereof, based on the total weight of the composition,
   ii. an adhesive component, which preferably forms an amorphous mass, comprising a crosslinked acrylic polymer and a non-crosslinked acrylic polymer in a ratio of 10 to 90 parts by weight to 90 to 10 parts by weight, and
   iii. 1 to 50% by weight of a penetration enhancer, based on the total weight of the composition, comprising a keto acid,
3) optionally at least one further adhesive layer, and
4) further optionally, a release liner.

In preferred embodiments, the transdermal drug delivery composition further comprises, a solubilizer and/or a tackifier.

The present invention further relates to a method of producing a transdermal therapeutic system comprising a backing layer, at least one adhesive layer and a release liner, comprising the steps of
1) preparing a solution comprising
   a. buprenorphine or a pharmaceutically acceptable salt thereof,
   b. a crosslinkable acrylic polymer,
   c. a non-crosslinkable acrylic polymer,
   d. a penetration enhancer, and
   e. optionally one or more of a solubilizer or tackifier,
2) coating the solution on the backing layer or on the release liner,
3) drying the coating to form the at least one adhesive layer, and coating the at least one adhesive layer with the release liner or the backing layer.

The present invention further relates to a TTS obtainable by the method according to the subject invention.

The transdermal therapeutic system of the present invention is useful as analgesic, in particular for treating a patient suffering from acute or chronic pain.

DETAILED DESCRIPTION OF THE INVENTION

The present invention provides a TTS for the transdermal delivery of buprenorphine. The TTS of the invention typically is a multi-layered system comprising at least one drug containing adhesive layer. The drug containing adhesive layer comprises or consists of a transdermal drug delivery composition comprising buprenorphine or buprenorphine analogue as active ingredient. The transdermal drug delivery composition further comprises an adhesive component of a crosslinked and a non-crosslinked acrylic polymer and a penetration enhancer comprising a keto acid.

In a preferred embodiment of the invention the adhesive component forms an amorphous mass. The term "amorphous" with respect to the adhesive component means that the adhesive component is free of acrylic polymer particles. Thus, the adhesive component typically forms a homogenous mass. The term "polymer particles" according to the present invention does not relate to the sphere formed due to the motion of polymer molecules, commonly designated as radius of gyration. Preferably, the adhesive component does not contain polymer particles of a median diameter of more than 10 µm or preferably more than 1 µm. More preferably, the adhesive component is free of polymer particles of a median diameter of more than 500 nm, still preferably, more than 200 nm, most preferably 50 nm or more. The polymer particle size can be measured by light microscopy for polymer particles having a particle size of more than 500 nm and scanning electron microscopy or transmission electron microscopy for particles having a particle size of 50 nm to 500 nm.

The amorphous adhesive component is generally formed of a solution of a crosslinkable and a non-crosslinkable acrylic polymer. In said solution the acrylic monomers are typically completely solved under visual inspection. Thus, the solution is free of non-solved polymer particles. More preferably, all ingredients of the solution are completely solved, and therefore form a homogenous solution.

Thus, in the method of producing a TTS of the present invention as described in detail further below, the solution comprising the drug forms an adhesive layer after coating and drying. Therein, the adhesive layer preferably forms an amorphous mass. Said amorphous mass is then typically free of discrete polymer particles. In contrast to the subject invention, when one dries an aqueous or non-aqueous dispersion or emulsion, such as described in EP 0 819 438 A2, the polymer forms a coalescent mass of observable polymer particles.

In a further preferred embodiment, the drug containing adhesive layer is described as forming a solid or semisolid mass, preferably having viscoelastic properties. Viscoelasticity in the context of the present invention means that the drug containing adhesive matrix has the property of materials that exhibit both viscous and elastic characteristics when undergoing deformation. Viscous materials resist shear flow and strain linearly with time when a stress is applied. Elastic materials strain instantaneously when stretched and just as quickly return to their original state once the stress is removed. Viscoelastic materials have elements of both of these properties and, as such, exhibit time dependent strain. Viscosity is the result of the diffusion of atoms or molecules inside an amorphous material.

Buprenorphine:

Buprenorphine relates to a compound represented by the following formula:

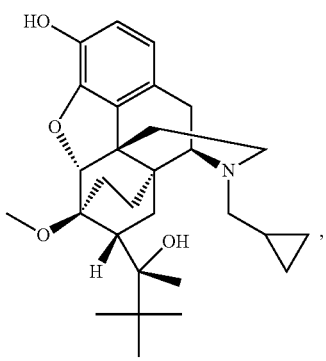 [SMILES: CO[C@]12CC[C@@]3(C[C@@H]1[C@](C)(O)C(C)(C)C)[C@H]1Cc4ccc(O)c5c4[C@@]3(CCN1CC1CC1)[C@H]2O5]

which has the IUPAC nomenclature of (2S)-2-[(−)-(5R,6R,7R,14S)-9α-cyclopropylmethyl-4,5-epoxy-6,14-ethano-3-hydroxy-6-methoxymorphinan-7-yl]-3,3-dimethylbutan-2-ol.

The term "buprenorphine" as used in the subject invention further comprises buprenorphine analogues such as buprenorphine salts, buprenorphine in its basic form or in its acid form. Preferably, buprenorphine is used in its basic form (buprenorphine base). Buprenorphine salts include, but are not limited to, salts such as the hydrochloride, sulphate, phosphate or its various organic acid salts such as maleate, succinate, mesylate and tosylate.

The active ingredient buprenorphine is contained in the transdermal drug delivery composition in an amount of 1 to 20% by weight based on the total weight of the composition. An amount of below 1% is not sufficient to induce analgesia whereas an amount of above 20% usually cannot be solved in the composition and further increases the risk of drug abuse due to the high concentration of the drug in the adhesive layer. The active ingredient is preferably contained in the transdermal drug delivery composition in an amount of 5 to 15% by weight, most preferably about 10% by weight based on the total weight of the composition.

Acrylic Polymer:

The transdermal drug delivery composition of the present invention further comprises an adhesive component. The adhesive component comprises a crosslinked and a non-crosslinked acrylic polymer, which are formed upon crosslinking of an adhesive component comprising a non-crosslinkable and a crosslinkable acrylic polymer.

The acrylic polymer of the drug containing adhesive layer is to provide the TTS with adhesive properties, thus enables adhesion of the TTS to the skin of a patient. In a preferred embodiment, a pressure sensitive adhesive (PSA) forms the adhesive layer. A pressure sensitive adhesive is an adhesive, which adheres to most substrates, such as the skin of a patient, with the application of pressure and generally remains tacky during the entire period of use of the PSA.

The drug delivery composition comprises the crosslinked acrylic polymer and the non-crosslinked acrylic polymer in a ratio of crosslinked:non-crosslinked of 90:10 to 10:90 parts by weight, preferably in a ratio of 85:15 to 50:50 parts by weight, further preferably in a ratio of 80:20 to 60:40 parts by weight, and more preferably in a ratio of 78:22 to 65:35 parts by weight, further more preferably between 76:24 to 67 to 33 parts by weight, most preferably in a ratio of about 70:30 parts by weight.

The adhesive component is formed from an adhesive composition comprising a non-crosslinkable and a crosslinkable acrylic polymer, in which the crosslinkable acrylic copolymer is crosslinked by a process as described further below. In the methods for preparing the adhesive layer of the TTS according to the subject invention, it is preferred that the crosslinkable acrylic polymer is crosslinked completely. Consequently, the above-mentioned ratio of crosslinked: non-crosslinked acrylic polymer present in the adhesive component formed upon crosslinking is regarded in the present invention as being equal with the ratio of the crosslinkable:non-crosslinkable acrylic polymer before crosslinking.

Suitable solvents for preparing a solution/dispersion of the acrylic polymers include, but are not limited to, organic solvents such as ethanol, ethyl acetate, 2-propanol, heptane, hexane, methanol, toluene, 2,4-pentandion and mixtures thereof.

Crosslinked Acrylic Polymer:

The crosslinked acrylic polymer is obtained by crosslinking a crosslinkable acrylic polymer. In a preferred embodiment, the crosslinkable acrylic polymer is a self-crosslinkable acrylic polymer, commonly also designated as self-curable acrylic polymer. The crosslinkable acrylic polymer contains reactive groups such as reactive acid groups, which take part in a crosslinking reaction to crosslink the crosslinkable (curable) acrylic polymer. Accordingly, the crosslinkable acrylic polymer might contain functional monomers and, additionally, non-functional monomers. In case the crosslinkable polymer is prepared from non-functional monomers, it is required to copolymerize the non-functional monomers with one or more monomers containing a functional group (functional monomers), which allows the acrylic polymer to take part in a crosslinking reaction.

A functional monomer in the context of the present invention usually refers to a polymerizable monomer containing a functional group. A functional group can be a reactive group, which allows the monomer to take part in a crosslinking reaction. In the cross-linking reaction the functional group reacts with another functional group to form a chemical bonding. A functional group includes, but is not limited to, a carboxy group, an epoxy group and a hydroxy group.

The crosslinked acrylic polymer is preferably a crosslinked acrylic copolymer, which includes, but is not limited to, random, linear or branched copolymers.

The crosslinked acrylic polymer to be used in the drug containing adhesive layer of the present invention can be obtained, for example, by using a (meth)acrylic acid alkyl ester, which is commonly used in acrylic polymer adhesives, as the main monomer component and copolymerizing it with a functional monomer. Generally, within this application the term (meth)acrylic acid either refers to acrylic acid or methacrylic acid.

Examples of the (meth)acrylic acid alkyl ester include (meth)acrylic acid alkyl esters having straight or branched-chain $C_{4-13}$ alkyl groups such as butyl, pentyl, hexyl, heptyl, octyl, nonyl, decyl, undecyl, dodecyl and tridecyl, and one or two or more (meth)acrylic acid alkyl esters can be used.

In addition, the (meth)acrylic acid alkyl ester is not particularly limited to the above examples, and a (meth) acrylic acid alkyl ester having a straight or branched-chain alkyl group of 1 to 13 carbon atoms or a (meth)acrylic acid alkyl ester having a straight or branched-chain alkyl group of 14 or more carbon atoms may be used in combination with a (meth)acrylic acid alkyl ester having a straight or branched-chain alkyl group of 4 to 13 carbon atoms. Examples of the further monomer copolymerizable with these (meth)acrylic acid alkyl esters include functional monomers and vinyl monomers.

Examples of the copolymerizable functional monomers include a carboxyl group-containing monomer such as (meth)acrylic acid, itaconic acid, maleic acid, maleic anhydride and crotonic acid, a sulfoxyl group-containing monomer such as styrenesulfonic acid, allylsulfonic acid, sulfopropyl (meth)acrylate, (meth)acryloyloxynaphthalene sulfonic acid, and acrylamide methylpropanesulfonic acid, a hydroxy group-containing monomer such as (meth)acrylic acid hydroxyethyl ester and (meth)acrylic acid hydroxypropyl ester, a (meth)acrylic acid alkoxyalkyl ester such as (meth)acrylic acid methoxyethyl ester and (meth)acrylic acid ethoxyethyl ester, an alkoxy group (or oxide bonding to side chain)-containing (meth)acrylic acid ester such as (meth)acrylic acid tetrahydrofurfuryl ester, (meth)acrylic acid methoxyethylene glycol ester, (meth)acrylic acid methoxydiethylene glycol ester and (meth)acrylic acid methoxypolyethylene glycol ester, and (meth)acrylonitrile. These monomers may be used alone or as a mixture of two or more to effect copolymerization.

Examples of the vinyl monomer include a vinyl ester such as vinyl acetate and vinyl propionate, and a vinyl monomer having a nitrogen atom-containing hetero ring such as N-vinyl-2-pyrrolidone, methylvinylpyrrolidone, vinylpyridine, vinylpiperidone, vinylpyrimidine, vinylpiperazine, vinylpyrazine, vinylpyrrole, vinylimidazole, vinylcaprolactam and vinyloxazole. These monomers may also be used alone or as a mixture of two or more to effect copolymerization.

One kind or two or more kinds of the functional monomers and vinyl monomers can be copolymerized with the (meth)acrylic acid alkyl ester, and it is desirable to use a carboxyl group-containing monomer, a hydroxy group-containing monomer, a (meth)acrylic acid alkoxyalkyl ester or an alkoxy group (or oxide bonding to side chain)-containing (meth)acrylic ester as the copolymerization component in the polymerization, because they have functional groups which become crosslinking points at the time of the crosslinking treatment. Preferably, the functional monomer is a carboxyl group-containing monomer or a hydroxy group-containing monomer. Moreover, the copolymerization component can improve cohesive force by increasing glass transition temperature of the acrylic polymer. In addition, when the improvement of cohesive force and drug solubility is taken into consideration, it is desirable to use vinyl esters or vinyl monomers having a nitrogen atom-containing hetero ring in the copolymerization.

In a preferred embodiment the crosslinked acrylic polymer is obtained from one or more monomers comprising a (meth)acrylic acid alkyl ester, a functional monomer comprising a carboxy group, an epoxy group and/or a hydroxy group, optionally a vinyl ester, or mixtures thereof.

The (meth)acrylic acid alkyl ester is preferably selected from butyl acrylate, 2-ethylhexyl acrylate, methyl acrylate and/or methyl methacrylate.

The functional monomer is preferably selected from acrylic acid, methacrylic acid, (meth)acrylic acid hydroxy alkylester, 2-hydroxylethyl acrylate and/or glycidyl methacrylate.

The vinyl ester is preferably selected from n-vinyl pyrrolidone and/or vinyl acetate.

The crosslinked acrylic polymer is most preferably obtained from monomers selected from acrylic acid, butyl acrylate, 2-ethylhexyl acrylate, 2-hydroxylethyl acrylate, glycidyl methacrylate, methyl acrylate, methyl methacrylate, n-vinyl pyrrolidone and vinyl acetate or mixtures thereof. In case the crosslinked acrylic polymer is obtained from the above listed preferred non-functional monomers, it is required that these monomers are copolymerized with one or more of a functional monomer, preferably acrylic acid and/or vinyl acetate.

In a preferred embodiment of the invention, the crosslinked acrylic polymer is present in the transdermal drug delivery composition in an amount of 5 to 60, preferably 20 to 50, more preferably 30 to 40 wt. %, preferably less than 40 wt. %, based on the total weight of the drug adhesive layer.

In a preferred embodiment the crosslinked acrylic polymer consists of 1 to 15 wt. %, most preferably about 5 wt. %, of acrylic acid, 5 to 25 wt. %, most preferably about 15 wt. %, of butyl acrylate, 60 to 90 wt. %, most preferably about 75 wt. %, of 2-ethylhexylacrylate and 1 to 15 wt. %, most preferably about 5 wt. %, of vinyl acetate, based on the total weight of the monomers.

In another preferred embodiment, the crosslinked acrylic polymer consists of 50 to 75 wt. %, most preferably about 68 wt. %, of 2-ethylhexylacrylate, less than 5 wt. %, most preferably less than 1 wt. %, of glycidyl methacrylate, 1 to 15 wt. %, most preferably about 5 wt. %, of 2-hydroxyethylacrylate and 15 to 40 wt. %, most preferably about 27 wt. %, of vinyl acetate, based on the total weight of the monomers.

In another preferred embodiment, the crosslinked acrylic polymer consists of 0.1 to 10 wt. %, most preferably about 3 wt. %, of acrylic acid, 65 to 90 wt. %, most preferably about 79 wt. %, of 2-ethylhexylacrylate and 10 to 30 wt. %, most preferably about 19 wt. %, of vinyl acetate, based on the total weight of the monomers.

Crosslinking

The crosslinking reaction for the preparation of a crosslinked acrylic polymer from a crosslinkable polymer can be effected by carrying out a physical and/or chemical crosslinking treatment.

In the physical treatment, preferably irradiation is applied, which can be radiation such as heat, ultraviolet rays or electron beam. In the chemical crosslinking treatment preferably a crosslinking agent is used. The crosslinking agent may be selected from a trifunctional isocyanate, a metal alcoholate comprised of titanium or aluminium or a metal chelate compound. Preferred crosslinking agents include aluminium acetyl acetonate and polybutyl titanate, most preferably polybutyl titanate. The amount of the crosslinking agent, which can be used in the chemical crosslinking reaction, is preferably from 0.01 to 2.0 parts by weight based on 100 parts by weight of the crosslinkable acrylic polymer.

Most preferably, crosslinking is achieved by using a self-crosslinkable acrylic polymer, which may be crosslinked upon drying the adhesive solution comprising the crosslinkable and the non-crosslinkable acrylic polymer. The term drying generally refers to a process wherein the acrylic polymer solution is exposed to ambient temperature or elevated temperature to remove the solvents. With respect to the most preferred acrylic polymers such as the DURO-TAK® polymers (National Starch and Chemical), these polymers are usually described as self-crosslinkable or self-curable. When using these polymers, crosslinking preferably occurs as a result of the drying process, thus by removal of the solvent. In addition, when the polymer solution is dried at elevated temperature crosslinking might not be complete immediately after the drying procedure due to the presence of residual solvent. In such a case, crosslinking can continue until the solvent has been removed completely. When exposing the acrylate adhesive to ambient temperature, crosslinking can thus continue for a few days, such as up to 3 to 7 days, until crosslinking is complete.

In the preferred case when crosslinking is performed by drying the acrylic polymer, the drying temperature is usually from 20° C. to 150° C., more preferably from 25° C. to 125° C., most preferably from 30° C. to 110° C. Drying is generally performed until the solvent is removed completely, typically for 1 to 180 min, preferably for 5 to 150 min, most preferably for 10 to 120 min. In further preferred embodiments, drying is achieved at a temperature of 30° C. to 100° C. for 30 to 120 min or at a temperature of 100° C. to 130° C. for 5 to 30 min.

In a further preferred embodiment of the invention, drying is performed with increasing temperature. For example, drying can be performed by increasing the temperature stepwise, preferably in two or three steps, such as initially drying at 20° C. to 50° C., then increasing the temperature to about 50° C. to 90° C. and finally to 80° C. to 120° C. Generally, drying may be achieved in a drying channel, preferably by exposing the adhesive solution to a stream of hot air, the air having the temperatures as described above.

In the present invention a combination of two or more of the aforementioned crosslinking methods can be used simultaneously or subsequently.

Non-Crosslinked Acrylic Polymer:

The non-crosslinked acrylic polymer is preferably a non-crosslinked acrylic copolymer and include, but are not limited to, random, linear or branched copolymers. The non-crosslinked acrylic polymer does not comprise functional groups, which take apart in a crosslinking reaction and can thus be described as a non-reactive acrylic polymer or a non-curing polymer.

In the context of the present invention the term "non-crosslinkable" and non-crosslinked" acrylic polymer can be used interchangeably. The term "non-crosslinkable acrylic polymer" is generally used for an acrylic polymer, which would not take apart in a crosslinking reaction, even in the presence of a crosslinking initiator or when applied to appropriate crosslinking conditions. The term "non-crosslinked acrylic polymer" is generally used in the present invention for an acrylic polymer, which is included in a polymer mixture in which a crosslinking reaction has occurred, without affecting the non-crosslinked acrylate.

The non-crosslinked acrylic polymer to be used in the drug containing adhesive layer of the present invention can be obtained, for example, by using a (meth)acrylic acid alkyl ester, which is commonly used in acrylic polymer adhesives, as the main monomer component and copolymerizing it with a further non-functional monomer(s) as listed under crosslinked polymers.

In a preferred embodiment, the non-crosslinked acrylic polymer is obtained from monomers comprising a (meth) acrylic acid alkyl ester, optionally an n-alkyl acrylamide, preferably a linear or branched n-alkyl acrylamide having 1 to 12 carbon atoms such as dimethyl (meth) acrylamide, tert-octyl acrylamide or N-butylacrylamide, and further optionally a vinyl ester, or mixtures thereof.

Most preferably, the non-crosslinked acrylic polymer is obtained by polymerizing monomers selected from 2-ethylhexyl acrylate, butyl acrylate, vinyl acrylate, methyl acrylate, t-octyl acrylamide, methyl methacrylate or mixtures thereof.

Typically, the non-crosslinked acrylic polymer is present in the drug delivery composition in an amount of 1 to 40, preferably 5 to 25, more preferably 10 to 20 wt. %, based on the total amount of the drug delivery composition.

In a further preferred embodiment, the non-crosslinked acrylic polymer is a random copolymer of 2-ethylhexyl acrylate, butyl acrylate, t-octyl acrylamide and methyl methacrylate.

Preferably, the non-crosslinked acrylic polymer is a random copolymer consisting of 20 to 45 wt. %, most preferably about 32 wt. % of 2-ethylhexyl acrylate, 20 to 45 wt. %, most preferably about 32 wt. % of butyl acrylate, 10 to 35 wt. %, most preferably about 20 wt. % of t-octyl acrylamide, and 5 to 25 wt. %, most preferably about 15 wt. % methyl methacrylate, all weight percentages based on the total weight of the monomers.

The polymeric reaction for producing the non-crosslinked acrylic polymer is preferably initiated by azobisisobutyronitrile. Residual monomers can be scavenged by t-amyloperoxipivalate.

Residual levels of starting monomers in the non-crosslinked acrylic polymer product are preferably 1000 ppm or below per monomer.

Penetration Enhancer:

The transdermal drug delivery composition of the subject invention further comprises one or more of a penetration enhancer. Since the skin presents a substantial barrier to ingress of foreign substances into the body, the art has recognized that the barrier to the transdermal delivery of an active ingredient through the skin can be overcome or reduced by incorporating excipients into the carrier that enhance the rate at which the active ingredient, i.e., the drug, passes, i.e., penetrates, through the skin. The term "enhancement" or "penetration enhancement" means an increase in the permeability of a biological membrane, such as the skin, to a drug, so as to increase the rate at which the drug permeates through the membrane and accelerate drug delivery.

An effective amount of penetration enhancer provides increased membrane permeability such as increased skin permeability, and thus provides increased rate of administration and amount of drug delivered through the skin. The term "penetration enhancer" relates to a substance or mixture of substances.

It was surprisingly found out in the present invention that a penetration enhancer comprising a keto acid such as 4-oxopentanoic acid or 5-oxohexanoic acid is particularly suitable to improve skin permeability and, at the same time, retains sufficient tackiness of the adhesive composition to ensure adhesion of the TTS over the whole period of use. Therefore, the combination of the adhesive composition containing the penetration enhancer according to the subject invention provides improved drug release without significantly reducing tackiness of the adhesive composition.

The penetration enhancer of the present invention comprises at least one keto acid. Preferably, the keto acid is represented by the general formula

$$R(CO)(CH_2)_nCOOH,$$

wherein R is $C_1$-$C_{18}$ alkyl, which can be linear, branched or cyclic, preferably linear $C_1$-$C_3$ alkyl, most preferably methyl, and n is from 1 to 6, preferably 2 or 3.

Particularly preferred keto acids are selected from 4-oxopentanoic acid (levulinic acid) and/or 5-oxohexanoic acid. In the most preferred embodiment, the penetration enhancer is 4-oxopentanoic acid.

In a further preferred embodiment, the transdermal drug delivery composition of the subject invention comprises a mixture of two or more penetration enhancers, wherein at least one of the penetration enhancers is a keto acid as described above. The one or more additional penetration enhancers are not particularly limited but are preferably selected from alkyl methyl sulfoxides, preferably decylmethyl sulfoxide, dimethyl sulfoxide; saturated fatty acids such as adipinic acid, caproic acid, caprylic acid, capric acid, myristic acid, lauric acid, stearic acid, palmitic acid, and alkyl esters thereof such as adipinic acid monoethylester; unsaturated fatty acids such as oleic acid, linoleic acid, linolenic acid, palmitoleic acid, and alkyl esters thereof, preferably oleyl oleate; saturated fatty alcohols such as myristyl alcohol, lauryl alcohol, stearyl alcohol, palmityl alcohol and cetyl alcohol; unsaturated fatty alcohols such as oleyl alcohol, palmitoleyl alcohol, elaidyl alcohol, linoleyl alcohol and linolenyl alcohol; azocyclo-alkan-2-ones, preferably 1-dodecylazacycloheptan-2-one; pyrrolidones such as 2-pyrrolidone, alkyl-2-pyrrolidone and N-methylpyrrolidone; glycols such as propylene glycol, polyethylene glycols, glycerol, dipropylene glycol, tripropylene glycol, diethylene glycol and triethylene glycol; alcohols, preferably ethanol, isopropyl alcohol, cyclohexanol; diethyltoluamide; tetrahydrofurfuryl alcohol; dimethyl formamide; dimethyl acetamide; 2,2,2-trichloroethanol; 2,2,2-trifluoroethanol; urea; salicylic acid; ethylene glycol monomethyl ether; N,N-dialkylhydroxylamine; 1,2-isopropylidene glycerol; N,N-dialkylnicotinamide; alkylaminooxide; hyaluronidase; isopropyl myristate; saccharose monooleate; lecithins; non-ionic surfactants; cholic acid; and derivatives thereof.

Preferred penetration enhancers are diacids such as adipinic acid or glutaric acid, its monoethyl esters such as adipinic acid monoethyl ester or glutaric acid monoethyl ester. Further preferred penetration enhancers are alkylic fatty acid esters of saturated and/or unsaturated fatty acids, each containing from 8-18 carbon atoms, such as isopropylpalmitate, oleyl oleate (Cetiol®) or isopropylmyristate. In a further preferred embodiment, the penetration enhancer is a mixture of levulinic acid and oleyl oleate.

The penetration enhancer is contained in the transdermal drug delivery composition in an amount of 1 to 50% by weight, preferably 15 to 35% by weight, based on the total weight of the composition.

In a preferred embodiment of the subject invention, the transdermal drug delivery composition contains 1 to 20 wt. %, more preferably 5 to 15 wt. %, of levulinic acid and 5 to 30 wt. %, more preferably 10 to 20 wt. %, of oleyl oleate.

Tackifier:

The transdermal drug delivery composition may further optionally comprise one or more tackifiers. Such tackifiers increase the adhesiveness of the adhesive layer. Tackifiers which may be used in the transdermal delivery agent according to the present invention include but are not limited to tackifiers selected from polybutenes; mineral oils; polysiloxanes; elastomeric and polymeric resins; terpene-based esters such as from β-pines; aromatic, aliphatic and alkylaromatic resins; melamine formaldehyde resins; phenolic resins; hydroabietyl alcohol; wood resins, preferably collophonium resin; or mixtures thereof. The most preferred tackifier is a wood resin ester such as collophonium ester, which can be hydrogenated. Hydrogenated collophonium resin is commercially available under the trademark Foral®.

The tackifier is preferably contained in the transdermal drug delivery composition in an amount of 1 to 30% by weight, preferably 5 to 20% by weight, based on the total weight of the composition.

Solubilizer and Additives:

The transdermal drug delivery composition may comprise further ingredients such as solubilizers, excipients, diluents, emollients, plasticizers, antiirritants, opacifiers, fillers, as well as other components or additives that are commonly formulated into a transdermal drug delivery composition.

The transdermal drug delivery composition may thus comprise constituents such as solubilizers. Typically, the function of the solubilizer is such that it acts as a crystallization inhibitor and/or that it increases the mechanical stability of the transdermal therapeutic system. Such solubilizers further increase the solubility of the pharmaceutically active agent in the transdermal drug delivery composition.

In a preferred embodiment of the invention, the solubilizer is present in the transdermal drug delivery composition in an amount of 1 to 30% by weight, preferably 5 to 15% by weight, based on the total weight of the composition.

Solubilizers which may be used in the transdermal drug delivery composition of the transdermal therapeutic system according to the present invention include but are not limited to soluble polyvinyl pyrrolidones as commercially available under the trademark Kollidon®. A soluble polyvinyl pyrrolidone is generally obtained by radical polymerization of N-vinyl pyrrolidone. Soluble polyvinyl pyrrolidone is also known as povidon(e), povidonum, polyvidone, poly(1-vinyl-2-pyrrolidone) and PVP.

Preferably, the solubilizer is a (preferably non-crosslinked) polyvinyl pyrrolidone having a weight average molecular weight $M_w$ of 1,000 to 3,000,000, more preferably from 100,000 to 2,000,000, most preferably from 1,000,000 to 1,500,000 as measured by light scattering.

The molecular weight of polyvinyl pyrrolidone (povidone) is usually expressed as the K-value. The polyvinyl pyrrolidone of the present invention preferably has a K-value of 10 to 100, most preferably from 80 to 95.

Further examples of such solubilizers include, but are not limited to, cyclodextrins and cyclodextrin derivatives such as substituted cyclodextrins; 2-(2-ethoxyethoxy)ethanol, urea, methyl 2-methylprop-2-enoate, neohesperidine, alcohols and polyols such as ethanol, isopropanol, butanol, benzyl alcohol, ethylene glycol, propylene glycol, octyldecanol, octyldodecanol, butanediols and isomers thereof, glycerol, pentaerythritol, sorbitol, mannitol, dimethyl isosorbide, polyethylene glycol, polypropylene glycol, polyvinylalcohol; hydroxypropyl methylcellulose and other cellulose derivatives; ethers of polyethylene glycols (PEG) having an average molecular weight of about 200 to about 6000, such as tetrahydrofurfuryl alcohol PEG ether (glycofurol) or methoxy PEG; amides such as 2-pyrrolidone, 2-piperidone, s-caprolactam, N-alkylpyrrolidone, N-hydroxyalkylpyrrolidone, N-alkylpiperid one, N-alkylcaprolactam, dimethylacetamide, and polyvinylpyrrolid one; esters, such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ϵ-caprolactone and isomers thereof, δ-valerolactone and isomers thereof, p-butyrolactone and isomers thereof; and other solubilizers known in the art, such as Eudragit® E100, dimethyl acetamide, dimethyl isosorbide, N-methylpyrrolidones, monooctanoin, diethylene glycol monoethyl ether, and water. Mixtures of solubilizers are also within the scope of the invention.

Preferred solubilizers include triacetin, triethylcitrate, ethyl oleate, ethyl caprylate, dimethylacetamide, N-methylpyrrolidone, N-hydroxyethylpyrrolidone, hydroxypropyl methylcellulose, hydroxypropyl cyclodextrins, ethanol, glycofurol, diethylene glycol monoethyl ether, propylene glycol, dimethyl isosorbide and polyvinyl pyrrolidone.

Particularly preferred solubilizers include sorbitol, glycerol, triacetin, ethyl alcohol, polyethylene glycol, glycofurol, propylene glycol and polyvinyl pyrrolidone, most preferably polyvinyl pyrrolidone.

The drug containing delivery composition may also further comprise fillers. Fillers which may be used in the transdermal drug delivery composition according to the present invention include but are not limited to silicon dioxide, metal oxides such as titanium dioxide or zinc dioxide, talc, silicates such as magnesium silicate or aluminium silicate, stearates such as zinc stearate, polyethylene, polystyrene, and mixtures thereof. Fillers may be contained in the drug containing delivery composition in an amount from 0 to 30 wt. %, preferably from 5 to 20% by weight, based on the total weight of the composition.

Transdermal Therapeutic Systems (TTS):

A transdermal therapeutic system according to the present invention typically comprises a backing layer, a drug containing adhesive layer and a release liner. The drug containing adhesive layer comprises or consists of a transdermal drug delivery composition. In a preferred embodiment, the drug containing adhesive layer consists of the transdermal drug delivery composition. The drug containing layer(s) usually are self-adhesive and can further be coated one or more additional adhesive layer(s). The transdermal therapeutic systems of the present invention are often referred to as matrix-controlled transdermal therapeutic systems or matrix TTS.

The TTS of the present invention typically comprise a backing layer, which usually is impermeable for the pharmaceutically active agent. The TTS of the present invention may further comprise one or more additional drug containing adhesive layers. The TTS may further comprise one or more further adhesive layers, which do not contain an active ingredient. The adhesive layer(s) thus may form one or more separate layers or be part of the drug containing layer(s). On the side, which is opposite to the backing layer the TTS generally comprises a release liner such as a peelable release liner.

Preferably, the drug containing adhesive layer is, on one side, affixed to the backing layer, and, on another side, to the release liner thus providing for a multi-layered design.

Backing Layer:

The backing layer is typically impermeable to the drug or other excipients. The backing layer is thus generally made of a material that is impermeable to the pharmaceutically active agent and other excipients of the matrix layer. The backing layer serves as a protective cover for the matrix layer and provides a support function. The backing layer can be formed so that it is essentially the same size as the matrix layer containing the pharmaceutically active agent. The backing layer can be of any appropriate thickness that will provide the desired protective and support functions. A suitable thickness is from about 5 µm to about 300 µm. More specifically, the thickness is less than about 150 µm, yet more specifically, it is less than about 100 µm, and most specifically, the thickness is less than about 50 µm. The thickness is further preferably more than 5 µm, more preferably more than 10 µm.

Examples of materials suitable for making the backing layer are films of acrylate, acrylonitrile-butadiene-styrene, acrylonitrile (methyl methacrylate) copolymer, acrylonitrile copolymer, ethylene ethyl acrylate, ethylene methyl acrylate, ethylene vinyl acetate, ethylene vinyl acetate copolymer, ethylene vinyl alcohol polymer, ionomers, nylon (polyamide), nylon (polyamide) copolymer, polybutylene, polycarbonate, polyester, polyethylene terephthalate, thermoplastic polyester copolymer, polyethylene copolymer (high density), polyethylene (high-molecular-weight, high density), polyethylene (intermediate-molecular weight, high density), polyethylene (linear, low density), polyethylene (low density), polyethylene (medium density), polyethylene oxide, polyimide, polypropylene, polypropylene (coated), polypropylene (oriented), polystyrene, polyurethane, polyvinyl acetate, polyvinyl chloride, polyvinylidene chloride and/or styrene-acrylonitrile. It is within the present invention that such films may be metallised or pigmented. Preferred materials for the manufacture of the backing layer are polyurethane, ethylene vinyl alcohol polymer and polyester.

Release Liner:

The release liner, which preferably is a peelable release liner, is to protect the adhesive, which mediates the attachment of the transdermal therapeutic system to the subject to which the TTS is applied. The release liner is thus to be removed from the transdermal delivery system prior to the application to the subject.

Release liners can be formed of polyester, polyethylene, polypropylene, polysiloxane, e.g. with a fluorosiliconized coating, polyacrylate, ethylene vinyl acetate, polyurethane, polyisobutene or paper. Preferably the paper is coated with silicone and/or polyethylene. In an embodiment, a foil consisting of polyethylene terephthalate is used, whereby, preferably, one side of such foil is siliconized. Typically, the thickness of such release liner is from 50 to 100 µm, preferably from 60 to 80 µm. Also a combination of any of the above materials may be used in the preparation of the release liner. The release liner preferably also comprises an adhesive, which may be one as defined herein.

Manufacture:

The TTS according to the present invention may be manufactured by preparing a solution of the ingredients as described above, coating the solution on the release liner, drying the coating to form the adhesive layer, and then optionally coating the adhesive layer with a backing layer. The features as described above for the transdermal therapeutic system and the drug containing delivery composition also apply for the manufacture of a TTS according to the present invention In the method of manufacture according to the present invention, the transdermal drug delivery composition forming the drug containing adhesive layer is generally prepared in a first step by mixing a non-crosslinkable acrylic polymer, a crosslinkable acrylic polymer, buprenorphine and optionally one or more of a solubilizer, penetration enhancer, tackifier or a further additive in an appropriate solvent. The ingredients are then mixed, for example by mechanically stirring the mixture. Stirring is preferably achieved until the acrylic polymers are completely solved under visual inspection. In a further preferred embodiment all ingredients are completely dissolved under visual inspection. Thus, the solution of the ingredients may be referred to as a homogenous solution.

Suitable solvents include, but are not limited to, organic solvents such as ethanol, ethyl acetate, 2-propanol, heptane, hexane, isopropyl alcohol, methanol, toluene, 2,4-pentandion and mixtures thereof. The drug containing solution/suspension is typically homogenized at a temperature between 20° C. and 25° C. Homogenization can be achieved by using a stirrer such as a magnetic stirrer.

In a further embodiment the drug and optional excipients are added to a suitable solvent and mixed to form a first solution/suspension. A second solution/suspension comprising the acrylic adhesive is then added to the first solution/suspension. The thus obtained mixture of the first and second solutions/suspensions is then further homogenized until the acrylic polymer and preferably all ingredients are solved completely to form a solution.

The solution is then preferably coated on a release liner. Preferably, the solution is applied to a siliconized side of a release liner. Such a release liner consists in the instant cases of a transparent foil such as a PET-foil. The coating is dried to remove the solvent and to form the drug containing adhesive layer.

The crosslinkable acrylic polymer is typically crosslinked upon drying to form a crosslinked polymer, wherein crosslinking and drying are performed as described above. Thus, the term crosslinkable acrylic polymer refers to an acrylic polymer, which has the function to take part in a crosslinking reaction. After crosslinking the crosslinkable acrylic polymer forms a crosslinked acrylic polymer. Since the drug containing adhesive layer is preferably formed from a solution in which the acrylic polymer and, more preferably, all ingredients are completely dissolved, the adhesive layer forms an amorphous mass as described above. In the method of producing a transdermal therapeutic system according to the subject invention, the coating is dried until the solvent is removed completely and therefore the crosslinking reaction is complete, i.e. the crosslinked acrylic polymer forms the crosslinked acrylic polymer.

In a further embodiment, the release liner is first coated with one or more adhesive layers, which do not contain an active ingredient, wherein the one or more adhesive layers are then coated with the drug containing adhesive layer of the invention.

The dried adhesive layer(s) are then supplied with a backing layer on the side, which is opposite to the release liner.

Alternatively, the drug containing homogenous solution is applied to a film, which acts as a backing layer e.g. a PET film such as Hostaphan® RN 19 is used as the backing layer, preferably a drug impermeable backing layer. The thus one-side coated backing layer is then usually dried as described above. Upon drying, the matrix layer containing the transdermal drug delivery composition is formed. The dried adhesive layer is then supplied with a release liner. The transdermal patches are subsequently punched from the thus obtained layered product.

The invention thus further refers to the transdermal therapeutic system obtainable by the above described methods of manufacture. All preferred embodiments and features as described above for the transdermal therapeutic system of the present invention thus also apply for the methods of manufacture of the TTS as described herein and the TTS obtainable by these methods.

The coating weight of the drug containing adhesive layer per unit area is typically between 40 and 150 g/m$^2$, preferably between 60 and 100 g/m$^2$, most preferably about 80 g/m$^2$.

The transdermal therapeutic system of the invention provides delivery of buprenorphine to a patient in need of the active ingredient. The TTS thus percutaneously releases the active ingredient in an amount, which is sufficient to induce analgesia. Preferably, the TTS of the present invention releases buprenorphine in an amount sufficient to obtain a constant blood plasma level of at least 100 pg ml, preferably of at least 200 pg/ml and up to a maximum of 600 pg/ml, preferably up to 1000 pg/ml. Buprenorphine is preferably released to the patient to achieve a constant blood plasma level for the entire period of administration, which generally is more then 24 hours, preferably more then 72 h. The TTS of the invention may be used to achieve a constant blood plasma level of buprenorphine up to 4 days, preferably up to 7 days.

The transdermal therapeutic system is used for treating analgesia in a patent. In particular, the transdermal therapeutic system is used for treating a patient suffering from acute or chronic pain.

DESCRIPTION OF FIGURES

The invention are further illustrated in FIGS. 1 and 2.

Figure 1:
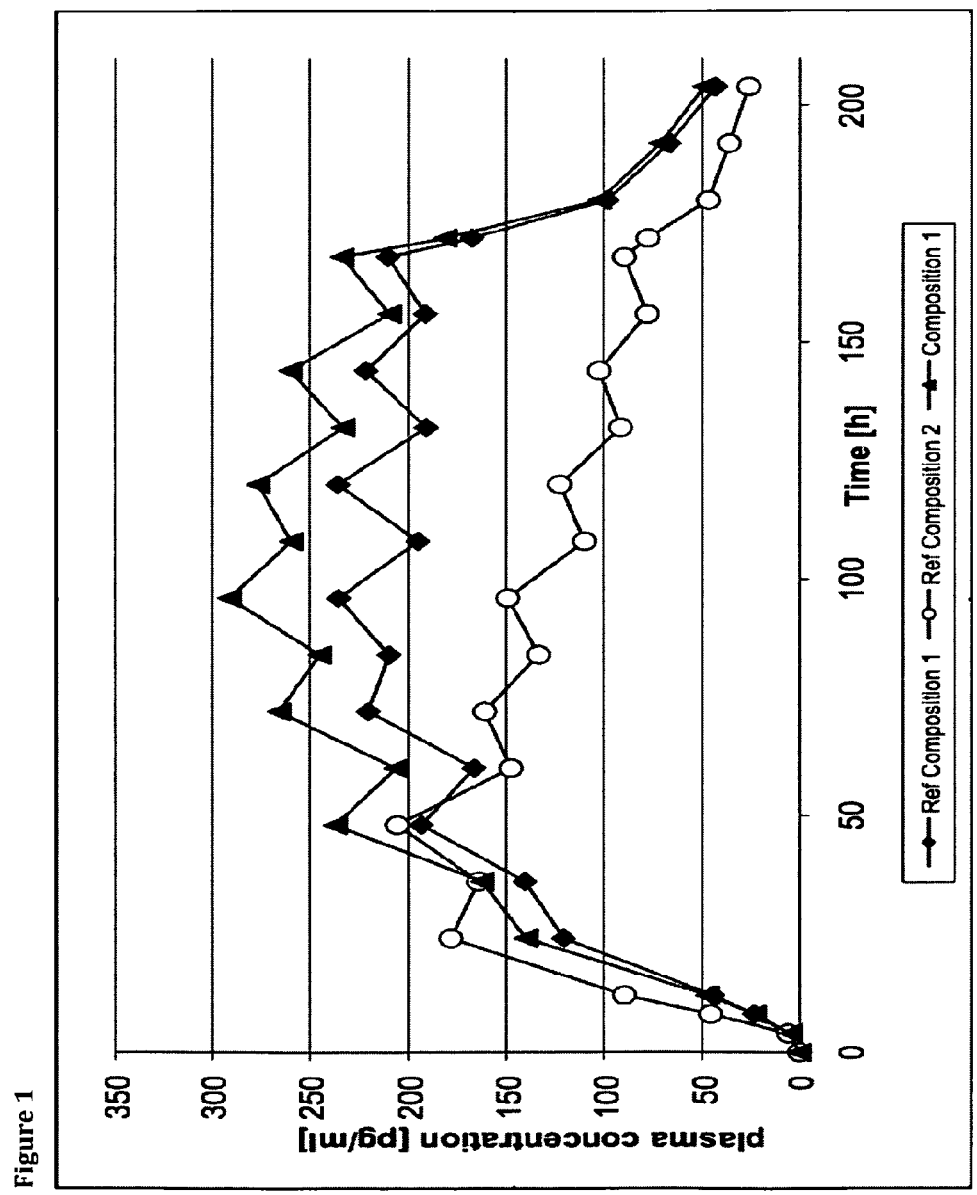
FIG. 1 shows buprenorphine blood plasma concentration in blood samples of patients wearing patches containing inventive and comparative buprenorphin compositions.

The invention will further be described in the following examples, which are included for purposes of illustrating the invention and are not intended, in any way, to be limiting of the scope of invention.

EXAMPLES

1) Manufacture of a Transdermal Therapeutic System

Example 1

48.125 g of a self-crosslinkable polyacrylate solution having a solid content of 48 wt. % and obtained from a monomer mixture comprising vinyl acetate, 2-ethylhexyl acrylate and acrylic acid in ethyl acetate, 2-propanol, heptane, toluol and 2,4-pentandion as solvents, 23.571 g of a non-crosslinkable polyacrylate solution having a solid content of 42 wt. % and obtained from 2-ethylhexyl acrylate, butyl acrylate, t-octyl acrylamide and methylmethacrylate solved in ethyl acetate, 6 g levulinic acid, 9 g oleyl oleate, 6 g polyvinyl pyrrolidone, 19.95 g 2-propanol, 39.98 g ethyl acetate and 6 g buprenorphine base were homogenized. It was stirred for about 2 h and controlled visually, whether all solids were solved. The homogenous solution was then coated on a transparent polyester foil of a width of 280 mm, resulting in a coating weight per unit area of about 80 g/m$^2$. The siliconized polyester layer served as a backing layer or as a release liner. The solvents were removed by drying with heated air, which was streamed over the wet coating. The adhesive coating was then covered with a polyester foil of a thickness of 15 μm. An area of 10 cm$^2$ was then cut by appropriate cutting tools. The edges between distinct systems were removed.

Example 2

55 g of a self-crosslinkable polyacrylate solution having a solid content of 48 wt. % and obtained from a monomer mixture comprising vinyl acetate, 2-ethylhexyl acrylate and acrylic acid as monomers in ethyl acetate 2-propanol, heptane, toluol and 2,4-pentandion as solvent, 15.741 g of a non-crosslinkable polyacrylate solution having a solid content of 42 wt. % and obtained from 2-ethylhexyl acrylate, butyl acrylate, t-octyl acrylamide and methylmethacrylate solved in ethyl acetate, 6 g levulinic acid, 9 g oleyl oleate, 6 g polyvinyl pyrrolidone, 19.95 g 2-propanol, 39.98 g ethyl acetate and 6 g buprenorphine base were homogenized. It was stirred for about 2 h and controlled visually, whether all solids were solved. The homogenous solution was then coated on a transparent polyester foil of a width of 280 mm, resulting in a coating weight per unit area of about 80 g/m$^2$. The siliconized polyester layer served as a backing layer or as a release liner. The solvents were removed by drying with heated air, which was streamed over the wet coating. The adhesive coating was then covered with a polyester foil of a thickness of 15 μm. An area of 10 cm$^2$ was then cut by appropriate cutting tools. The edges between distinct systems were removed.

Example 3

48.125 g of a self-crosslinkable polyacrylate solution having a solid content of 48 wt. % and obtained from a monomer mixture comprising vinyl acetate, 2-ethylhexyl acrylate and acrylic acid in ethyl acetate, 2-propanol, heptane, toluol and 2,4-pentandion as solvents, 23.571 g of a non-crosslinkable polyacrylate solution having a solid content of 42 wt. % and obtained from 2-ethylhexyl acrylate, butyl acrylate, t-octyl acrylamide and methylmethacrylate solved in ethyl acetate, 6 g 5-oxohexanoic acid, 9 g oleyl oleate, 6 g polyvinyl pyrrolidone, 19.95 g 2-propanol, 39.98 g ethyl acetate and 6 g buprenorphine base were homogenized. It was stirred for about 2 h and controlled visually, whether all solids were solved. The homogenous solution was then coated on a transparent polyester foil of a width of 280 mm, resulting in a coating weight per unit area of about 80 g/m². The siliconized polyester layer served as a backing layer or as a release liner. The solvents were removed by drying with heated air, which was streamed over the wet coating. The adhesive coating was then covered with a polyester foil of a thickness of 15 µm. An area of 10 cm² was then cut by appropriate cutting tools. The edges between distinct systems were removed.

2) Evaluation of Buprenorphine Release from TTS Patches and Evaluation of Adhesive Force The following commercially available compounds have been used in the following Examples:

Kollidon 90 F®: a non-crosslinked polyvinyl pyrrolidone available from BASF.

Cetiol PH®: oleyl oleate available from Cognis Europe.

The crosslinked acrylic polymer was obtained from a monomer mixture comprising acrylic acid, 2-ethylhexyl acrylate and vinyl acetate, supplied in a solvent mixture of ethyl acetate, heptane, isopropylalcohol, toluene and 2,4-pentanedion containing 0.4% of aluminium acetyl acetonate as crosslinker.

The non-crosslinked acrylic polymer was obtained from a monomer mixture comprising 2-ethylhexyl acrylate, butyl acrylate, t-octyl acrylamide and methyl methacrylate, supplied in ethyl acetate as solvent.

Transdermal therapeutic buprenorphine systems (also designated in the following as "patches") were prepared according to the method of manufacture as described for Example 1 (all percentages are on a weight basis).

Compositions 1 and 2 were according to the subject invention, thus, the adhesive component of the transdermal drug delivery composition forming the drug containing adhesive layer included a mixture of a crosslinked and a non-crosslinked acrylic polymer. Moreover, the adhesive component formed an amorphous mass.

The resulting compositions were as described in Table 1:

156, 168 (following patch removal), 172, 180, 192, and 204 hours. Blood samples were analyzed for buprenorphine concentration levels and are as shown in FIG. 1.

It can be seen by FIG. 1 that the TTS according to the invention (Composition 1) leads to increased blood plasma concentrations of the active ingredient compared to the comparative TTS (Reference Compositions 1 and 2). In particular, the TTS of the invention releases buprenorphine in an amount sufficient to obtain a blood plasma level of at least 100 pg ml over a period of more than 144 h and a blood plasma level of at least 200 pg ml over a period of more than 96 h. The Reference Composition 1 comprising only cross-linked acrylic polymer as single adhesive component and levulininc acid as enhancer shows significantly reduced blood plasma concentrations. Thus, it was surprisingly found by the inventors that the combination of a crosslinked and a non-crosslinked acrylic polymer in the drug adhesive layer leads to enhanced blood plasma levels of the active ingredient. Moreover, the Reference Composition 2 having AMEE instead of levulinic acid enhancer merely reaches a maximum buprenorphine blood plasma concentration of 200 pg/ml, which is much lower than in Reference Composition 1 or the inventive Composition 1. In addition the maximum blood plasma concentration rapidly decreases after only 50 h of skin adhesion. Thus, it was not possible with the Reference Composition 2 to reach a constant blood plasma concentration of buprenorphine.

It could thus be surprisingly shown by the present invention that the TTS of the subject invention lead to higher plasma levels of buprenorphine in the blood plasma of patients which remains constant over the required period of time of 3 or 4 to 7 days and which is sufficient to induce analgesia in a patient.

2.2 In Vitro Evaluation of Buprenorphine Skin Permeation

Skin permeation was evaluated using Compositions 1 and 2 and Reference Compositions 3 and 4 as show in Table 1. Skin permeation measurements were performed according to "ECD Guidelines for the Testing of Chemicals/Section 4: Health Effects, Test No. 428: Skin Absorption: in vitro

TABLE 1

|  | Composition 1 | Composition 2 | Reference Composition 1 | Reference Composition 2 | Reference Composition 3 | Reference Composition 4 |
| --- | --- | --- | --- | --- | --- | --- |
| Buprenorphine | 10% | 10% | 10% | 10% | 10% | 10% |
| Enhancer 1 | 10% levulinic acid | 10% levulinic acid | 10% levulinic acid | 10%, AMEE[1] | 12.5% caprylic acid monoglyceride | 20% caprylic acid monoglyceride |
| Enhancer 2 | 15% Cetiol ® PH | 15% isopropyl myristate | 15% Cetiol ® PH | 15% Cetiol ® PH | 12.5% isopropyl myristate | 20% isopropyl myristate |
| Solubilizer | 10% Kollidon ® 90 F | 10% Kollidon ® 90 F | 10% Kollidon ® 90 F | 10% Kollidon ® 90 F | 10% Kollidon ® 90 F | 5% silicate |
| acrylic polymer adhesive | 55% crosslinked/ non-crosslinked[2] | 55% crosslinked/ non-crosslinked[2] | 55% crosslinked | 55% crosslinked | 55% crosslinked/ non-crosslinked[2] | 55% crosslinked/ non-crosslinked[2] |

[1]Adipinic acid monoethyl ester
[2]ratio crosslinked: non-crosslinked acrylic polymer was 70:30 on a weight basis 2.1 In Vivo Studies for Evaluation of Buprenorphine Blood Plasma Concentrations Samples of patches of Composition 1 and Reference Compositions 1 and 2 were used in a single-center, randomized, single-dose, four-treatment, four-period crossover study. Healthy adult subjects were randomly assigned to one of 4 treatment sequences. There was a washout period of 14 days between treatment arms. The system was removed 168 hours after application. Blood samples (1×5 ml) were collected in blood collection tubes containing heparin sodium before patch application and at the following times thereafter: 4, 8, 12, 24, 36, 48, 60, 72, 84, 96, 108, 120, 132, 144, method; OECD; published by: OECD Publishing, 2004".
Preparation of skin permeation cells were as follows:

| | |
| --- | --- |
| Cell | Vertical diffusion cell |
| Medium | PBS buffer, pH 5.6 |
| Permeation area | 1 cm² |
| Acceptor volume | 40 ml |
| Sample volume/replacement | 1 ml/automatically |
| Sampling | After 6, 12, 24, 36, 48, 60, 72, 84, 96, 120, 144 and 168 h |

-continued

| | |
|---|---|
| Membrane | Dermatomised human skin |
| Temperature of water bath | 32° C. |

The samples were analyzed for buprenorphine using conventional high performance liquid chromatography (HPLC) methods.

| | |
|---|---|
| Column | Hypersil ® BDS C8, 250 × 4.0 mm, 5 μm |
| Mobile phase | 58% 10 mM KH$_2$PO$_4$, pH 3.0/42% acetonitrile |
| Flow rate | 1 ml/min |
| Detector | UV detector, wave length 210 mm |

Figure 2:
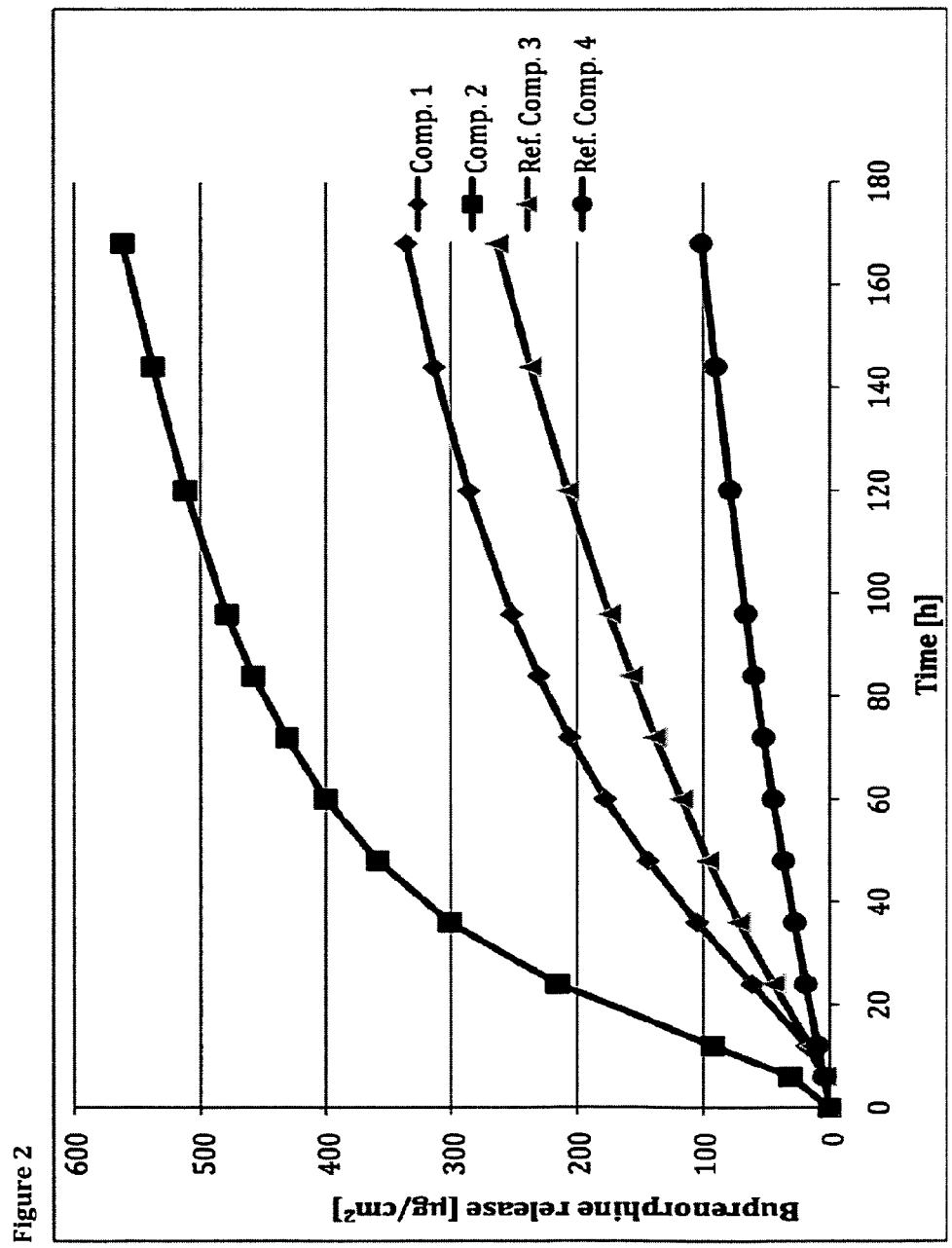
FIG. 2 shows a comparison of in vitro buprenorphine skin permeation through dermatomised human skin of inventive and comparative compositions.

The cumulative amount of buprenorphine penetrating through the skin was calculated and reported as μg/cm$^2$. The results of the measurements are shown in FIG. 2 as average values. Four samples were measured from each batch of Compositions 1 and 2 and Reference Compositions 3 and 4. However, only three of four measurements could be considered for Reference Composition 3.

Based on the above-results as shown in FIG. 2, the buprenorphine flux could be calculated. The buprenorphine flux corresponds to the amount of buprenorphine penetrating the dermatomised skin per hour reported in μg/(cm$^2$*h), as shown in Table 2:

| | Com-position 1 | Com-position 2 | Reference Composition 3 | Reference Composition 4 |
|---|---|---|---|---|
| Flux [μg/(cm$^2$h)] | 2.25 | 2.52 | 1.71 | 0.66 |

2.3 Adhesive Force Measurements

Adhesive force was determined using Compositions 1 and 2 and Reference Compositions 3 and 4 as show in Table 1. Adhesive force measurements were performed according to A.F.E.R.A. method 4001 in which peel test was carried out at 90° peel using stainless steel. Results were as shown in Table 3:

| | Com-position 1 | Com-position 2 | Reference Composition 3 | Reference Composition 4 |
|---|---|---|---|---|
| Adhesive force [N] | 0.8 | 1.3 | 2.2 | (—)* |

*could not be determined due to adhesive composition remaining partially on the release liner upon peeling FIG. 2 surprisingly shows that skin permeation was significantly higher for Compositions 1 and 2 compared with Reference Compositions 3 and 4. These results could be confirmed by the corresponding flux values, which were also significantly higher for Compositions 1 and 2 compared with Reference Compositions 3 and 4. Both compositions 1 and 2 show a satisfactory adhesive force which is strong enough to provide tackiness over the whole period of use and which can easily be removed from the skin of the patient. In particular, Composition 2 has the benefits of providing high tackiness and a high buprenorphine release.

In contrast, adhesive force for Reference Composition 4 could not be determined since the adhesive composition was too soft and remained partially on the release liner upon peeling. Thus, no meaningful results could be obtained. Moreover, although Reference Composition 3 shows a high adhesive force and the results of the buprenorphine release and flux values were much lower compared with the inventive compositions.

Therefore, only the Compositions 1 and 2 provide a satisfactory balance between buprenorphine release, flux and adhesive force, making the patches particularly suitable to provide a constant and high buprenorphine release over a period of more than three days, and preferably four days.

Further, the combination of the adhesive composition comprising a crosslinked and a non-crosslinked acrylic acid polymer and containing the penetration enhancer according to the subject invention provides improved drug release while at the same time ensures sufficient tackiness of the adhesive composition to provide strong adhesion but also comfortable wear of the TTS.

In summary, the invention provides a transdermal system having one or more of the benefits of (1) a long lasting (more than three days, preferably more than four days) and continuous release of active ingredient,
(2) good tolerability by the skin over the entire period of use,
(3) reliable efficacy,
(4) preventing abuse of the drug contained in the transdermal system,
(5) good comfort even after the entire period of use,
(6) inexpensive production with a highly reproducibly quality,
(7) the dosage can be adjusted by simply varying the size of the skin-contact area,
(8) high stability in storage, and
(9) high mechanical stability due to the homogeneous structure of the system.

The invention claimed is:

1. A transdermal therapeutic system comprising:
   1) a backing layer,
   2) at least one drug containing adhesive layer containing a transdermal drug delivery composition consisting of:
      i. 5 to 15% by weight of buprenorphine, based on the total weight of the composition,
      ii. an adhesive component, which preferably forms an amorphous mass, comprising 20 to 50% by weight of a crosslinked acrylic polymer and 5 to 25% by weight of a non-crosslinked acrylic polymer, based on the total weight of the composition, in a ratio of 80 to 20 parts by weight to 60 to 40 parts by weight,
      iii. and 5 to 15% by weight of levulinic acid, based on the total weight of the composition,
      iv. 10 to 20% by weight of oleyl oleate, based on the total weight of the composition, and
      v. 5 to 15% by weight of polyvinyl pyrrolidone, based on the total weight of the composition; and
   3) optionally at least one further adhesive layer, and
   4) further optionally, a release liner,
   wherein the crosslinked acrylic polymer is obtained from one or more non-functional monomers and one or more functional monomers, the functional monomer comprising a carboxy group, an epoxy group and/or a hydroxy group,
   wherein the transdermal therapeutic system releases buprenorphine in an amount sufficient to achieve a constant blood plasma of at least 200 pg/ml for up to 4 days.

2. The transdermal therapeutic system according to claim 1, wherein the functional monomer is selected from the group consisting of acrylic acid, methacrylic acid, (meth)acrylic acid hydroxy alkylester, 2-hydro-xylethyl acrylate and glycidyl methacrylate.

3. The transdermal therapeutic system according to claim 1, wherein the non-crosslinked acrylic polymer is obtained from monomers comprising one or more (meth)acrylic acid alkyl esters, optionally one or more of a n-alkyl acrylamide, and further optionally one or more of a vinyl ester, or mixtures thereof.

4. The transdermal therapeutic system according to claim 3, wherein:
- the (meth)acrylic acid alkyl ester is selected from the group consisting of 2-ethylhexyl acrylate, butyl acrylate, methyl acrylate and methyl methacrylate,
- the monomers further comprise an n-alkylacrylamide comprising t-octyl acrylamide, and
- the monomers further comprise a vinyl ester comprising vinyl acrylate.

5. The transdermal therapeutic system according to claim 1, wherein the crosslinked acrylic polymer and the non-crosslinked acrylic polymer are present in a ratio of crosslinked : non-crosslinked of 78:22 to 65:35 parts by weight.

6. The transdermal therapeutic system according to claim 1, wherein the crosslinked acrylic polymer and the non-crosslinked acrylic polymer are present in a ratio of crosslinked : non-crosslinked of 76:24 to 67:33 parts by weight.

7. The transdermal therapeutic system according to claim 1, wherein the crosslinked acrylic polymer and the non-crosslinked acrylic polymer are present in a ratio of crosslinked : non-crosslinked of about 70:30 parts by weight.

* * * * *